(12) United States Patent
Nemoto et al.

(10) Patent No.: US 8,177,757 B2
(45) Date of Patent: *May 15, 2012

(54) CHEMICAL LIQUID INJECTION SYSTEM

(75) Inventors: Shigeru Nemoto, Tokyo (JP); Takashi Saitoh, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 1389 days.

This patent is subject to a terminal disclaimer.

(21) Appl. No.: 11/720,189

(22) PCT Filed: Jun. 9, 2005

(86) PCT No.: PCT/JP2005/010585
§ 371 (c)(1),
(2), (4) Date: May 24, 2007

(87) PCT Pub. No.: WO2006/057089
PCT Pub. Date: Jun. 1, 2006

(65) Prior Publication Data
US 2007/0260194 A1    Nov. 8, 2007

(30) Foreign Application Priority Data
Nov. 26, 2004 (JP) ................. 2004-342881

(51) Int. Cl.
*A61M 5/00* (2006.01)
*A61M 5/178* (2006.01)
*B29B 9/00* (2006.01)

(52) U.S. Cl. .................. 604/181; 604/213; 264/13

(58) Field of Classification Search .............. None
See application file for complete search history.

(56) References Cited

U.S. PATENT DOCUMENTS
7,455,659 B2 * 11/2008 Nemoto et al. ............ 604/152

FOREIGN PATENT DOCUMENTS
| | | |
|---|---|---|
| JP | 09-122234 | 5/1997 |
| JP | 2000-507473 | 6/2000 |
| JP | 2002-11096 | 1/2002 |
| JP | 2002-102343 | 4/2002 |
| JP | 2003-290346 | 10/2003 |
| WO | WO 97/36635 | 10/1997 |

OTHER PUBLICATIONS
International Search Report for PCT/JP2005/010585.

* cited by examiner

*Primary Examiner* — Nicholas Lucchesi
*Assistant Examiner* — Pritesh Patel
(74) *Attorney, Agent, or Firm* — Knobbe Martens Olson & Bear LLP

(57) ABSTRACT

A piston adapter, which can be easily removed even when it is mounted on a piston member of a rodless syringe and pressed in a cylinder member, is provided. In piston adapter 200, when manual operation member 230 is manually rotated relative to adapter rod 210, adapter shaft 220 is also rotated to turn the trailing end of flange engagement member 240 engaging with an engagement open/close mechanism near leading end of the flange engagement member, thereby piston adapter 200 can be easily put on and removed from the piston member of the rodless syringe its leading end by manually operating the trailing end of piston adapter 200.

24 Claims, 10 Drawing Sheets

CHEMICAL LIQUID INJECTION SYSTEM

CROSS REFERENCE TO RELATED APPLICATIONS

This application claims benefit of and priority to and is a U.S. National Phase of PCT International Application Number PCT/JP2005/10585, filed on Jun. 9, 2005, designating the United States of America, which claims priority under U.S.C. §119 to Japanese Application 2004-342881 filed on Nov. 26, 2004. The disclosures of the above-referenced applications are hereby incorporated by this reference in their entirety.

TECHNICAL FIELD

The present invention relates to a chemical liquid injection system for injecting a liquid into a patient from a normal syringe with a chemical liquid injector, and more particularly, to a chemical liquid injection system on which a rodless syringe can be mounted on a chemical liquid injector by means of a piston adapter.

BACKGROUND ART

Presently available imaging diagnostic apparatuses for capturing diagnostic images of patients include CT (Computed Tomography) scanners, MRI (Magnetic Resonance Imaging) apparatuses, PET (Positron Emission Thmography) apparatuses, ultrasonic diagnostic apparatuses, angiography apparatuses, MRA (MR angiography) apparatuses and the like.

When the abovementioned imaging diagnostic apparatuses are used, a liquid such as a contrast medium or physiological saline may be injected into a patient. Chemical liquid injectors for automatically performing the injection have been put into practical use. An example of such a chemical liquid injector in the related art will hereinafter be described with reference to FIGS. 8 to 10.

As shown in FIG. 8, normal syringe 10 serving as a liquid syringe comprises cylinder member 11 and piston member 12. Cylinder member 11 includes elongated cylinder body 13 in a cylindrical shape. Cylinder body 13 has a closed leading end face having hollow conduit 14 formed at the center and a trailing end having cylinder flange 15 on the outer circumference.

Piston member 12 includes elongated piston rod 17 which has piston flange 18 formed on the outer circumference of the trailing end. Piston head 19 made of an elastic member such as rubber and resin is put on the leading end of piston rod 17 and piston head 19 is slidably inserted into the interior of cylinder member 11.

Chemical liquid injector 20 illustrated herein includes one injection head 21 and two piston driving mechanisms 22. One injection head 21 has two concave portions 23 formed therein for individually holding cylinder members 11 of two normal syringes 10. Two piston driving mechanisms 22 are placed individually in the rearward section of two concave portions 23 and hold and slide piston members 12 of normal syringes 10.

More specifically, as shown in FIG. 9, piston driving mechanism 22 includes slide rod 25 slidable forward and rearward. Piston pressing member 26 is formed integrally with the front end of slide rod 25 and abuts on piston member 12 from behind. A pair of engagement hooks 27 openable or closable leftward and rightward is placed on piston pressing member 26. Engagement hooks 27 individually catch the left and right of the front surface of piston flange 19.

There are a plurality of types of normal syringes 10 to be mounted on chemical liquid injector 20. Since such normal syringes 10 of the various types have components of different sizes or shapes, the chemical liquid injection system illustrated herein includes cylinder adapter 30 prepared for each of normal syringes other than that of the maximum size.

Cylinder adapter 30 is formed to have the outer shape comparable to that of cylinder member 11 of normal syringe 10 of the maximum size and has adapter flange 31 formed on the outer circumference of the trailing end in the same shape as that of cylinder flange 15 of normal syringe 10 of the maximum size. Concave portion 23 of injection head 21 accommodates cylinder member 11 of normal syringe 10 of the maximum size and cylinder adapter 30 which are placed in the same manner. Cylinder adapter 30 accommodates cylinder member 11 of normal syringe 10 of the size fitting concave portion 32 of that cylinder adapter 30.

Besides the abovementioned normal syringe 10, rodless syringe 40 as shown in FIG. 10 is an example of the liquid syringe. In rodless syringe 40, piston member 41 comprises a piston head having no piston rod. Piston flange 42 having a small diameter is formed directly on the trailing end of the piston head.

Since normal syringe 10 typically has piston flange 18 formed to have a larger diameter than the internal diameter of cylinder member 11, piston pressing member 26 of chemical liquid injector 20 for holding piston flange 18 of normal syringe 10 is formed to have a larger diameter than the internal diameter of cylinder member 11.

Thus, piston pressing member 26 of chemical liquid injector 20 cannot enter cylinder member 11 of rodless syringe 40 and cannot press directly piston member 41 of rodless syringe 40. When such rodless syringe 40 is mounted on chemical liquid injector 20, piston adapter 50 connects piston member 41 to piston driving mechanism 22.

Piston adapter 50 includes adapter rod 51 having an about the same shape as that of piston member 12 of normal syringe 10 and has adapter flange 52 formed on the trailing end and having the same shape as that of piston flange 16. Piston adapter 50 has recess 53 formed at the leading end and receiving piston flange 42 of rodless syringe 40. Flange holding member 54 is put to be swingable for opening or closing recess 53.

In chemical liquid injector 20 of the related art with the abovementioned structure, normal syringe 10 of the maximum size is directly mounted on injection head 21, and normal syringe of a size other than the maximum size is mounted on injection head 21 with dedicated cylinder adapter 30 placed between them. Rodless syringe 10 is mounted on injection head 21 with dedicated piston adapter 50 and, as required, cylinder adapter 30 placed between them.

In use of rodless syringe 40, flange holding member 54 of piston adapter 50 is manually operated to open recess 53 to insert piston flange 42 into recess 53, and then flange holding member 54 is manually operated to close recess 53. Piston adapter 50 is mounted on piston member 41 in this manner to cause them to have an about the same outer shape as that of normal syringe 10, so that rodless syringe 40 can be put on injection head 21 of chemical liquid injector 20, such as by using cylinder adapter 30 or the like, similarly to normal syringe 10.

In this case, cylinder member 11 of rodless syringe 40 is held in concave portion 23 of injection head 21 with cylinder adapter 30 placed between them, and adapter flange 52 of piston adapter 50 connected to piston member 41 is held by piston driving mechanism 22.

Cylinder member 11 is connected to a patient through an extension tube (not shown), and piston adapter 50 is pressed by piston driving mechanism 22. Piston member 41 is pressed into cylinder member 11 together with piston adapter 50 to inject the liquid into the patient from cylinder member 11.

There are a pre-filled type and a refill type in the above-mentioned normal syringe 10 and rodless syringe 40. The pre-filled type is shipped with a liquid contained therein and is used only once. The refill type is filled with a desired liquid by an operator and is repeatedly used. In normal syringe 10 and rodless syringe 40 of the pre-filled type, after piston members 12, 41 are pressed into cylinder member 11 for liquid injection, piston members 12, 41 do not need to be pulled out. Thus, it is easy to press piston members 12, 41 into cylinder member 11 in liquid syringes 10, 40 of the pre-filled type, but it is often difficult to pull them out.

Chemical liquid injectors of the type described above have been invented and applied by the present applicant (see, for example, patent documents 1 and 2). Piston adapters of the type described above also have been invented and applied by the present applicant (see, for example, patent document 3).

Patent document 1: Japanese Patent Laid-Open No. 2002-11096
Patent document 2: Japanese Patent Laid-Open No. 2002-102343
Patent document 3: Japanese Patent Laid-Open No. 2003-290346

DISCLOSURE OF THE INVENTION

Subject to be Solved by the Invention

Above described chemical liquid injector 20 can inject the liquid from normal syringe 10 to the patient, and can also make use of roddless syringe 40 by using piston adapter 50.

In piston adapter 50, however, flange holding member 54 for releasably holding piston flange 42 is located at the leading end of piston rod 51, so that flange holding member 54 cannot be manually operated when piston rod 51 is inserted in cylinder member 11 of rodless syringe 40 for liquid injection.

Thus, in rodless syringe 40 of the pre-filled type, piston member 41 pressed into cylinder member 11 is not pulled out therefrom. Piston adapter 50 cannot be removed from rodless syringe 40 after the completion of liquid injection. Inevitably, currently available piston adapter 50 is a disposable component as well as rodless syringe 40.

For example, if the extension tube connecting the patient to rodless syringe 40 is removed, and piston adapter 50 is pulled out from the trailing end of cylinder member 11 together with piston member 41, it is not impossible to remove piston adapter 50 from rodless syringe 40.

In rodless syringe 40 of the pre-filled type, however, it is easy to press piston member 41 into cylinder member 11 but it is often difficult to pull it out as described above. It is actually difficult to remove piston adapter 50 from rodless syringe 40, and even if piston member 41 is easily pulled out, that work is complicated. In addition, since flange holding member 54 should be manually operated to open or close recess 53 in holding and releasing piston flange 42 in piston adapter 50 described above, that work is complicated.

The present invention has been made in view of the above-mentioned problems, and it is an object thereof to provide a chemical liquid injection system in which a piston adapter is mounted on a piston member of a rodless syringe and inserted into a cylinder member and then can be easily removed therefrom.

Means to Solve the Subject

A chemical liquid injection system according to the present invention includes a chemical liquid injector, a rodless syringe, and a piston adapter. The piston adapter includes an adapter rod, a Range holding mechanism, a manual operation member, and an operation interlocking mechanism. The chemical liquid injector includes a piston driving mechanism formed to hold and slide a piston flange of a normal syringe. The normal syringe includes a piston member and a syringe member. The piston member has a piston head mounted at the leading end of an elongated piston rod and has the piston flange formed on the outer circumference of the trailing end. The cylinder member is formed in an elongated shape and has an opening at its trailing end into which the piston member is inserted slidably. The rodless syringe includes an elongated cylinder member and a piston member slidably inserted into the cylinder member from the opening at the trailing end thereof. The piston member does not have a piston rod and has a piston flange directly formed at the trailing end of a piston head. The piston adapter is formed in an elongated shape and connects the piston flange of the rodless syringe to the piston driving mechanism of the chemical liquid injector.

The piston adapter includes an adapter rod, an adapter shaft, a manual operation member, a flange engagement member, an engagement supporting mechanism, and an engagement open/close mechanism. The adapter rod is formed in an elongated, hollow shape having an adapter flange formed on the outer circumference of the trailing end and held by the piston driving mechanism. The adapter shaft is formed in an elongated shape and placed inside the adapter rod and rotatable about an axis having the same direction as that of the adapter rod. The manual operation member is connected to the trailing end of the adapter shaft and rotatably exposed near the trailing end of the adapter rod. The flange engagement member is formed in an elongated shape releaseably engaging with the piston flange of the rodless syringe. The engagement supporting mechanism pivotably supports the trailing end of the flange engagement member about the axis direction at a position protruded outward from the leading end of the adapter shaft. The engagement open/close mechanism is connected to the leading end of the adapter rod and engages with the flange engagement member near the leading end thereof.

In a piston adapter of a chemical liquid injection system according to a second aspect of the present invention, an engagement supporting mechanism pivotably supports the trailing end of a flange engagement member about the axis direction near the outer circumference of the leading end of an adapter rod. An engagement open/close mechanism engages with the flange engagement member near the leading end thereof at a position protruded outward from the leading end of an adapter shaft.

Thus, in the piston adapter of the chemical liquid injection system of the present invention, when the manual operation member is manually rotated relative to the adapter rod, the adapter shaft and the engagement supporting mechanism are also rotated to turn the trailing end of the flange engagement member engaging with the engagement open/close mechanism near the leading end of the flange engagement member, thereby the flange engagement member is opened or closed to the axis of the adapter rod.

Various means referred to in the present invention may be arranged to perform their functions, and may comprise dedicated hardware for performing a predetermined function, a data processing apparatus whose predetermined function is given by a computer program, a predetermined function performed in a data processing apparatus according to a computer program, or a combination thereof.

Various means referred to in the present invention do not need to be a separate entity. A plurality of components may be constructed as one member, a single component may be constructed by a plurality of members, a certain component may be part of another component, or a certain component may have a portion overlapping a portion of another component.

Effect of the Invention

In the piston adapter of the chemical liquid injection system according to the present invention, when the manual operation member is manually rotated relative to the adapter rod, the adapter shaft and the engagement supporting mechanism are also rotated to turn the trailing end of the flange engagement member engaging with the engagement open/close mechanism near the leading end of the flange engagement member, thereby the flange engagement member is opened or closed to the axis of the adapter rod. The manual operation on the trailing end of the piston adapter allows the leading end thereof to be mounted on or removed from the piston member of the rodless syringe. Even when the piston adapter is used for the rodless syringe of the pre-filled type in which the piston member is easily pressed into the cylinder member but is not easily pulled out, the piston adapter can be easily removed from the rodless syringe and be used repeatedly.

DESCRIPTION OF REFERENCE NUMERALS

Figure 1:
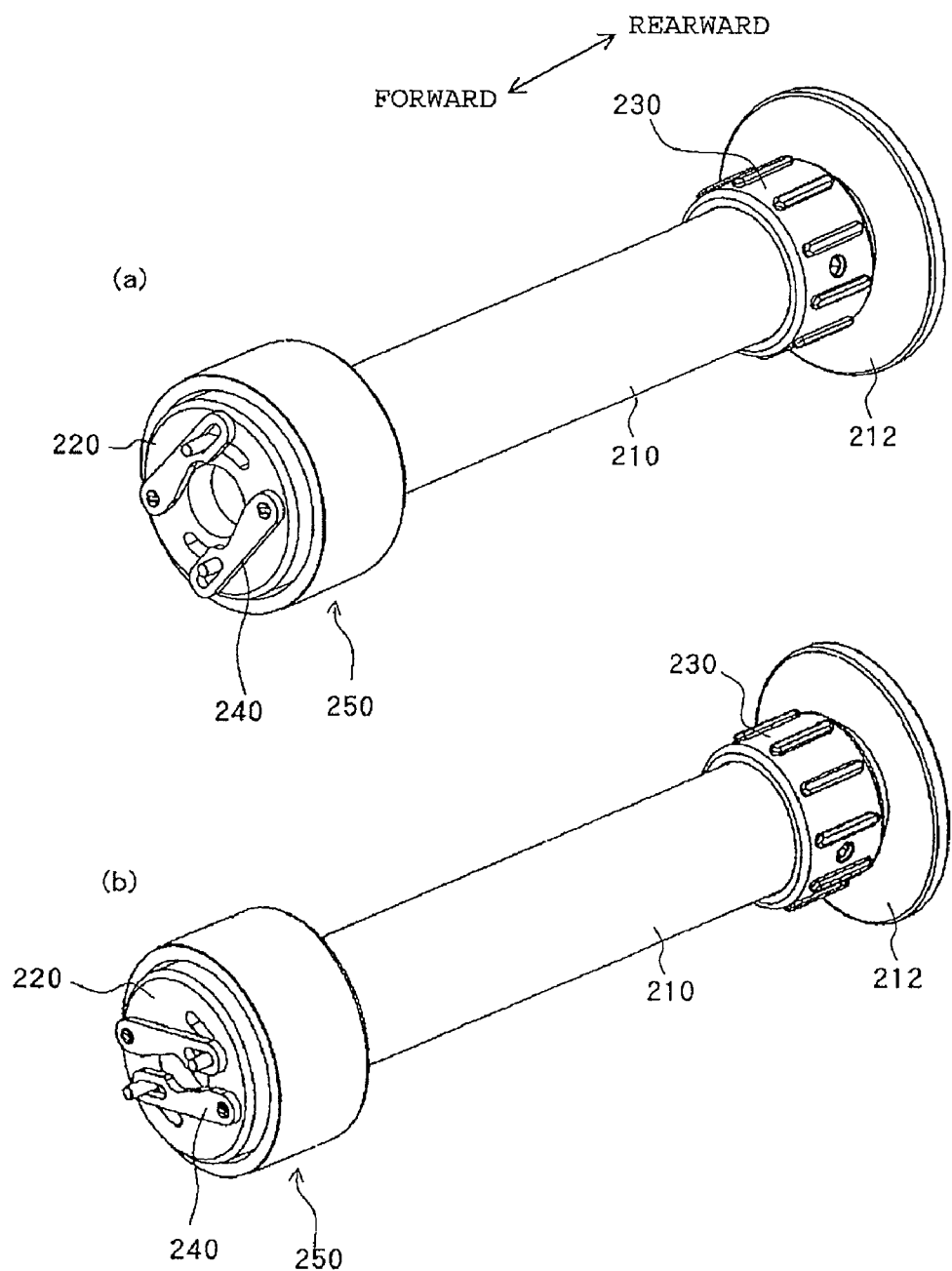
FIG. 1 is a perspective view showing the operation of the main portions of a piston adapter of a chemical liquid injection system in an embodiment of the present invention.
Figure 2:
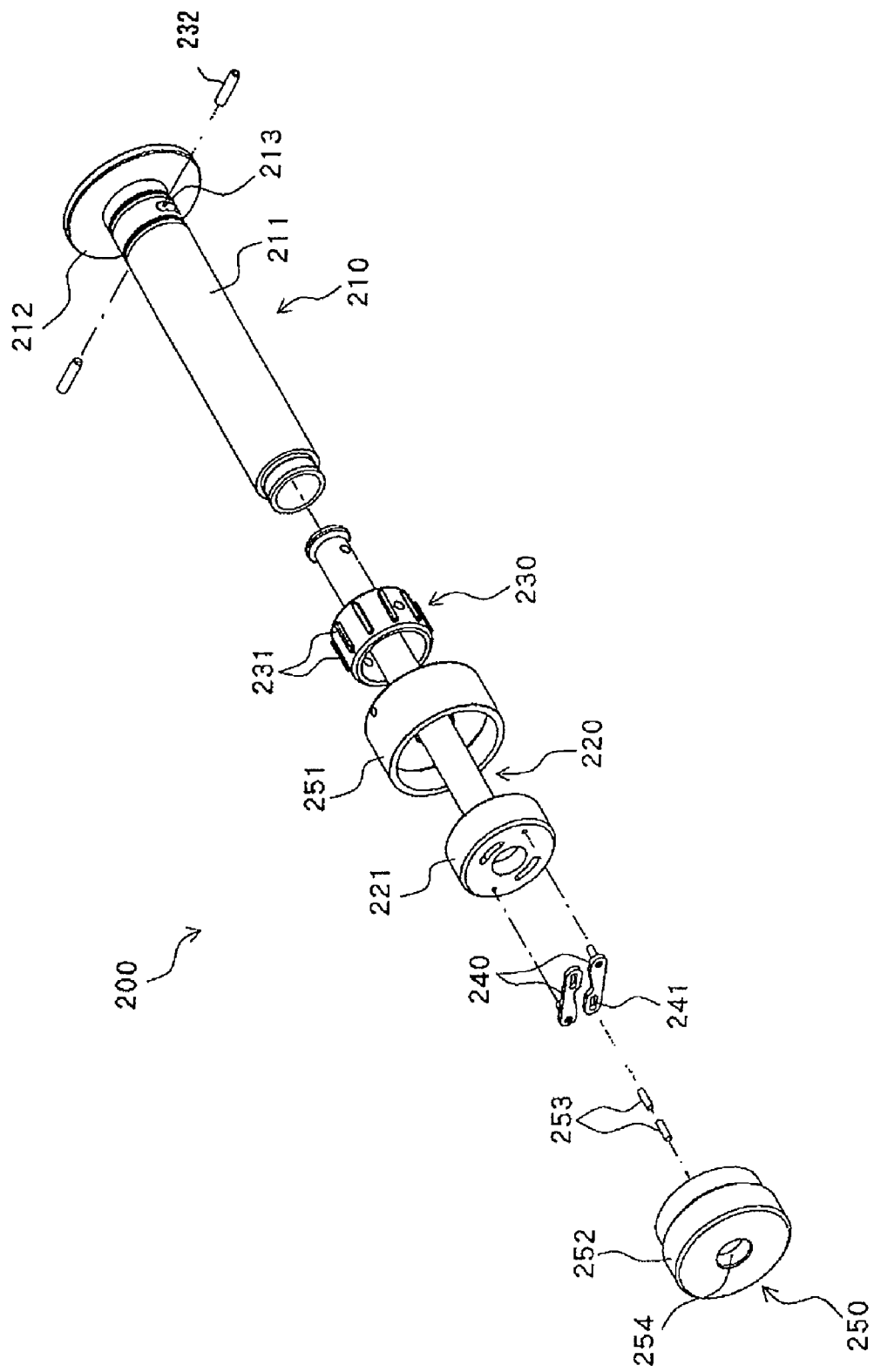
FIG. 2 is an exploded perspective view showing the structure to be assembled of the piston adapter.
Figure 3:
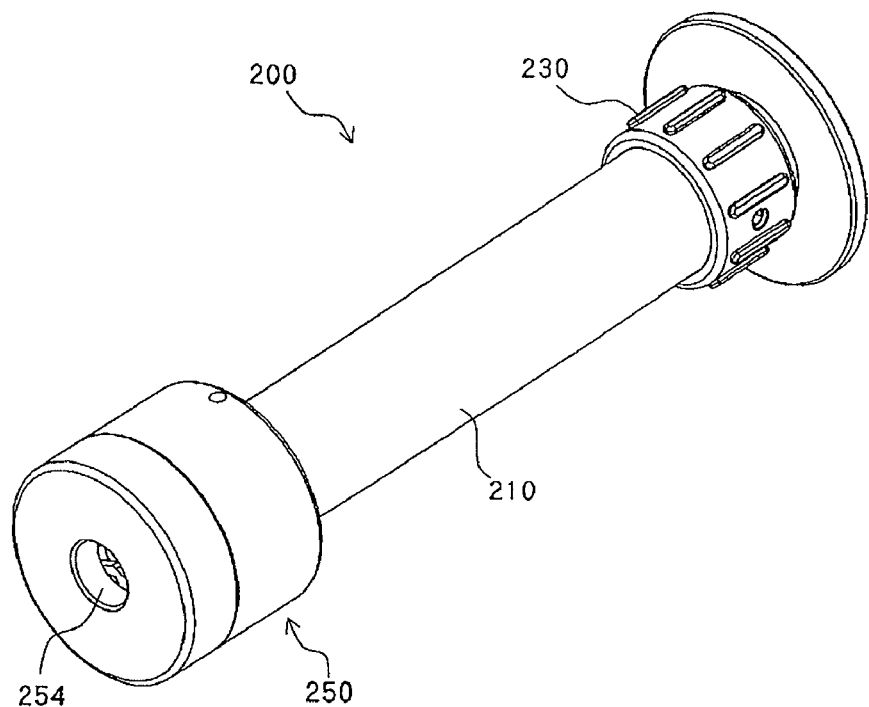
FIG. 3 is a perspective view showing the outer appearance of the piston adapter.

10 NORMAL SYRINGE
11 CYLINDER MEMBER
12, 41 PISTON MEMBER
17 PISTON ROD
18, 42 PISTON FLANGE
22 PISTON DRIVING MECHANISM
40 RODLESS SYRINGE
100 CHEMICAL LIQUID INJECTOR
200, 400 PISTON ADAPTER
210, 420 ADAPTER ROD
212 ADAPTER FLANGE
220 ADAPTER SHAFT
221 DISCORD PORTION serving as engagement supporting mechanism
230, 410 MANUAL OPERATION MEMBER
240 FLANGE ENGAGEMENT MEMBER
250 ENGAGEMENT OPEN/CLOSE MECHANISM
253 ENGAGEMENT PIN serving as slide engagement member
411, 412 CONCAVE PORTION
430 BALL PLUNGER serving as engagement holding mechanism

BEST MODE FOR CARRYING THE INVENTION

An embodiment of the present invention will hereinafter be described with reference to the drawings. In the embodiment, the same components as those in the related art described above are designated with same names, and detailed description thereof will be omitted.

Configuration of Embodiment

An embodiment of the present invention will hereinafter be described with reference to FIGS. 1 to 7. In the embodiment, the same components as those in the related art described above are designated with same names and reference numerals, and detailed description thereof will be omitted. Although the directions of forward, rearward, up, down, left, and right are specified as shown in the embodiment, these directions are defined for convenience to simply describe the relative relationship between components of the present invention and the definition does not limit any direction in manufacture or actual use when the present invention is implemented.

Figure 7:
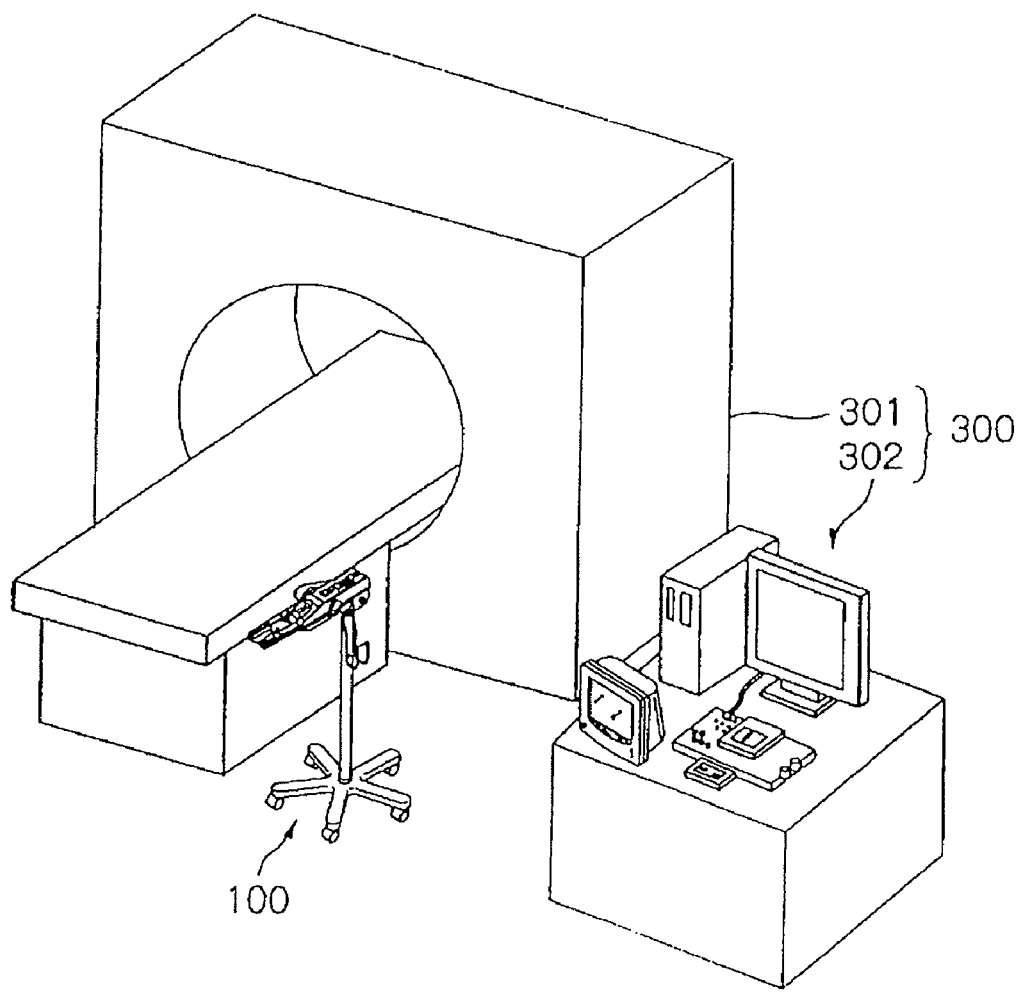
FIG. 7 is a perspective view showing the outer appearance of an MRI apparatus serving as an imaging diagnostic apparatus.
Figure 8:
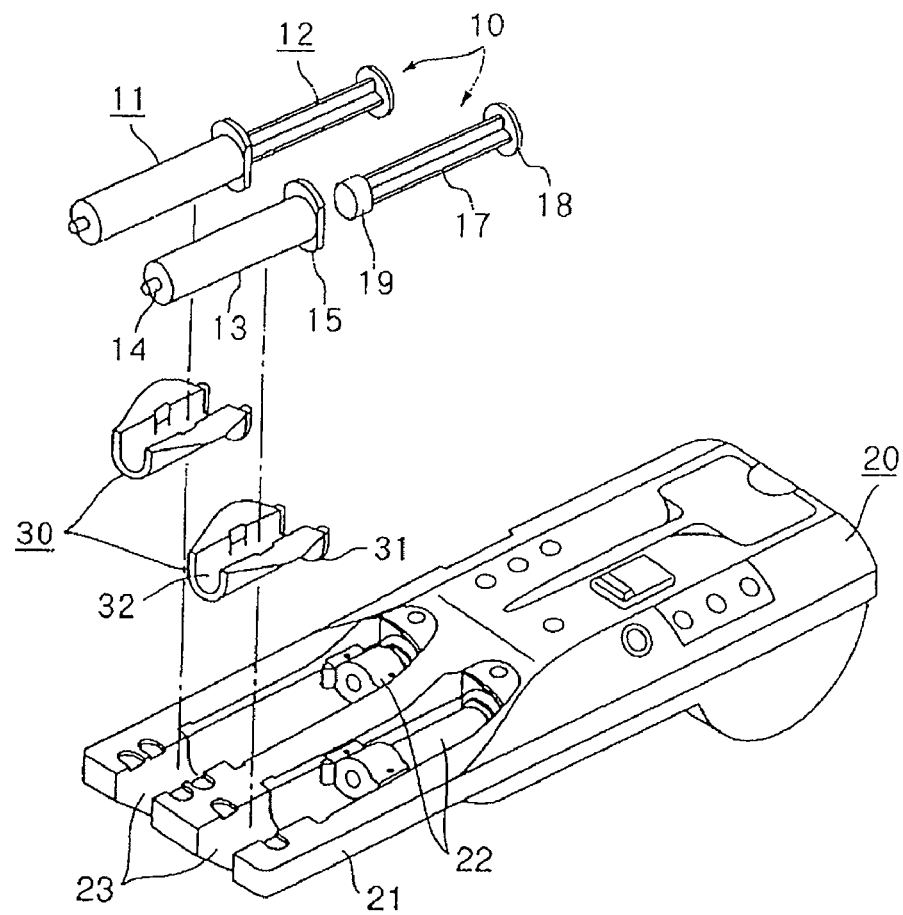
FIG. 8 is a perspective view showing the outer appearance of an injection head and a normal syringe of a chemical liquid injector in the related art.
Figure 9:
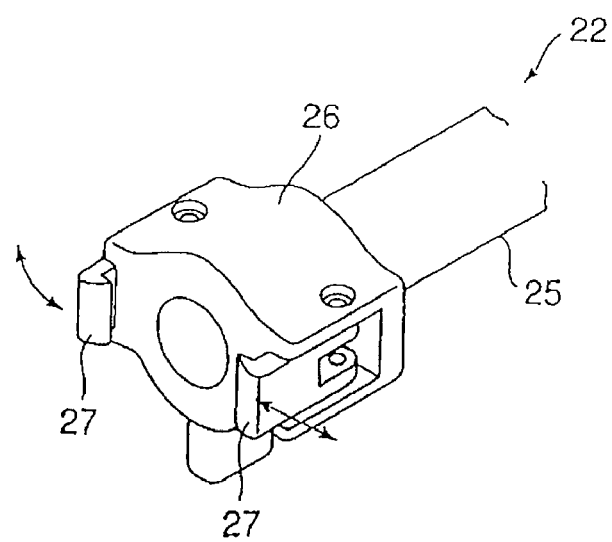
FIG. 9 is a perspective view showing the outer appearance of the main portions of a piston driving mechanism.
Figure 10:
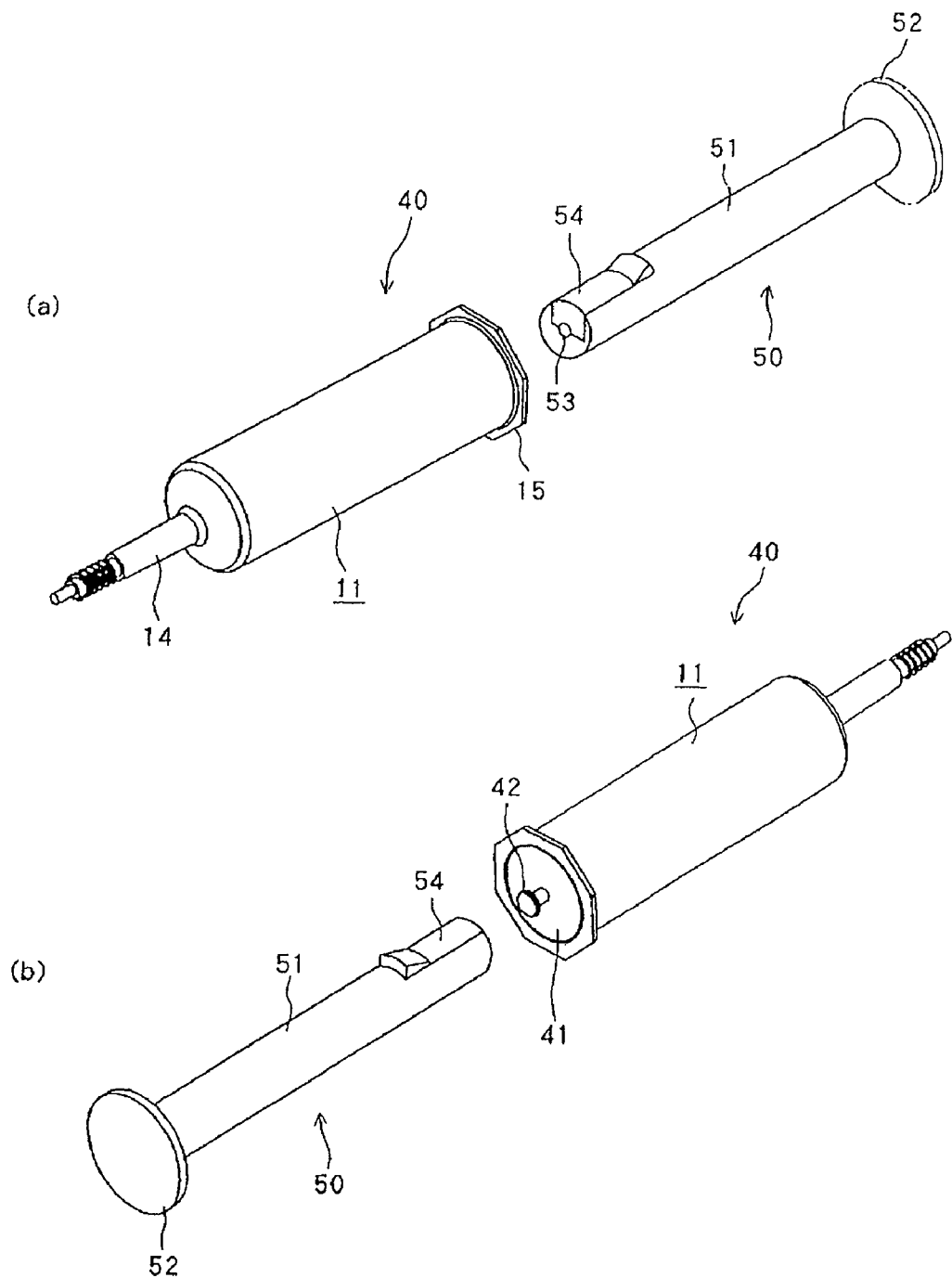
FIG. 10 is a perspective view showing the outer appearance of a piston adapter and a rodless syringe.

A chemical liquid injection system of the embodiment comprises chemical liquid injector 100, normal syringe 11, rodless syringe 40, piston adapter 200 and the like, and is used to inject a contrast medium into a patient (not shown) whose diagnostic image is taken by MRI apparatus 300, for example. As shown in FIG. 7, MRI apparatus 300 includes imaging unit 301 for shooting a diagnostic image from a patient and control unit 302 for controlling the operation of imaging unit 301 and displaying the shot diagnostic image.

Figure 6:
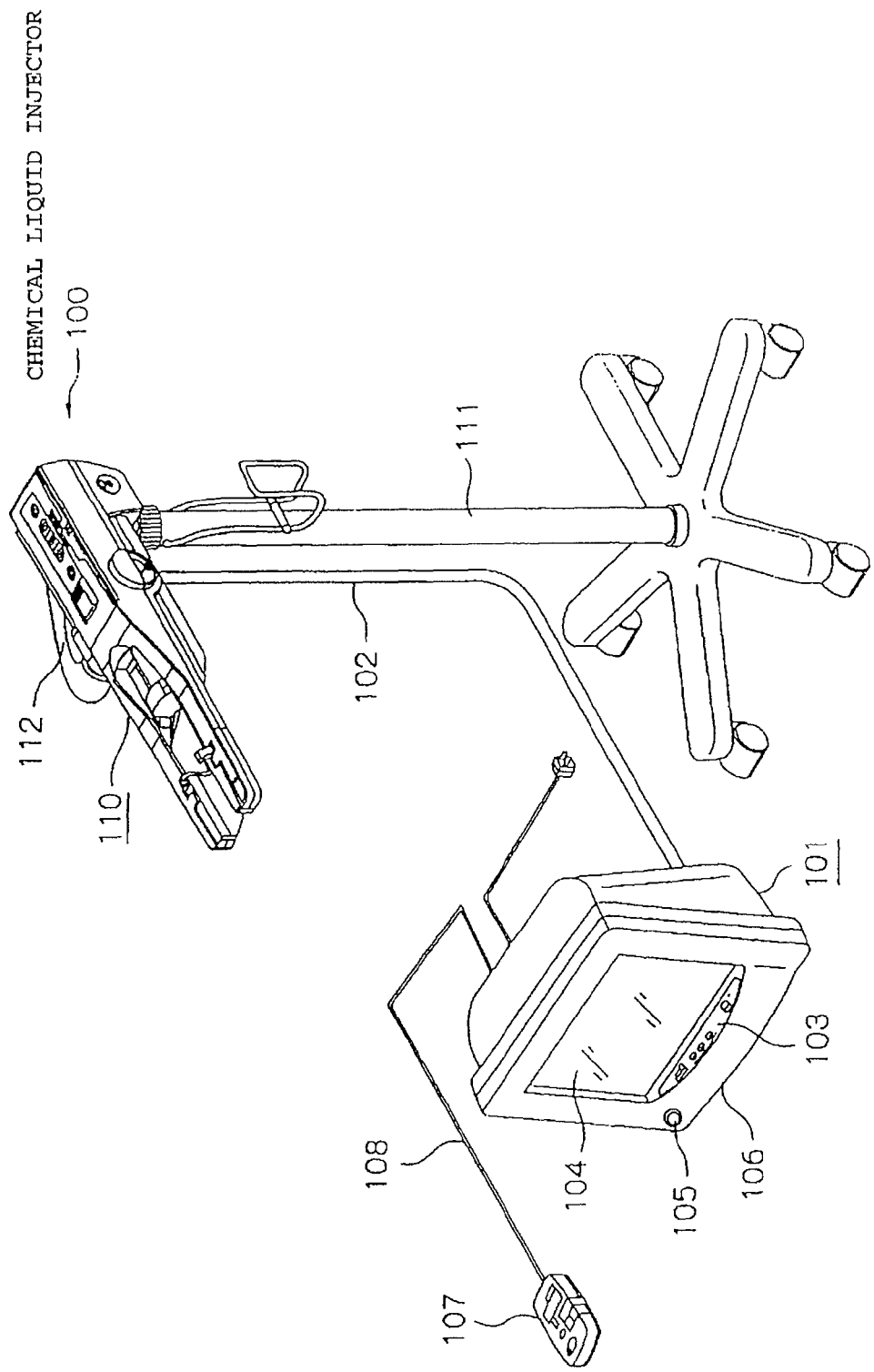
FIG. 6 is a perspective view showing the outer appearance of the chemical liquid injector.

As shown in FIG. 6, chemical liquid injector 100 of the embodiment has injection apparatus body 101 and injection head 110 constructed as separate components which are wire-connected through communication cable 102. Injection head 110 drives normal syringe 10 mounted thereon to inject a liquid into a patient. Injection apparatus body 101 controls the operation of injection head 110.

Injection apparatus body 101 has operation panel 103, touch panel 104 serving as a display panel, speaker unit 105 and the like, all of which are disposed on the front face of unit housing 106. Injection apparatus body 101 is wire-connected to controller unit 107 as a separate component through connector 108. Injection apparatus body 101 contains a computer unit (not shown) and is wire-connected to control unit 302 of MRI apparatus 300 via a communication network (not shown).

Figure 5:
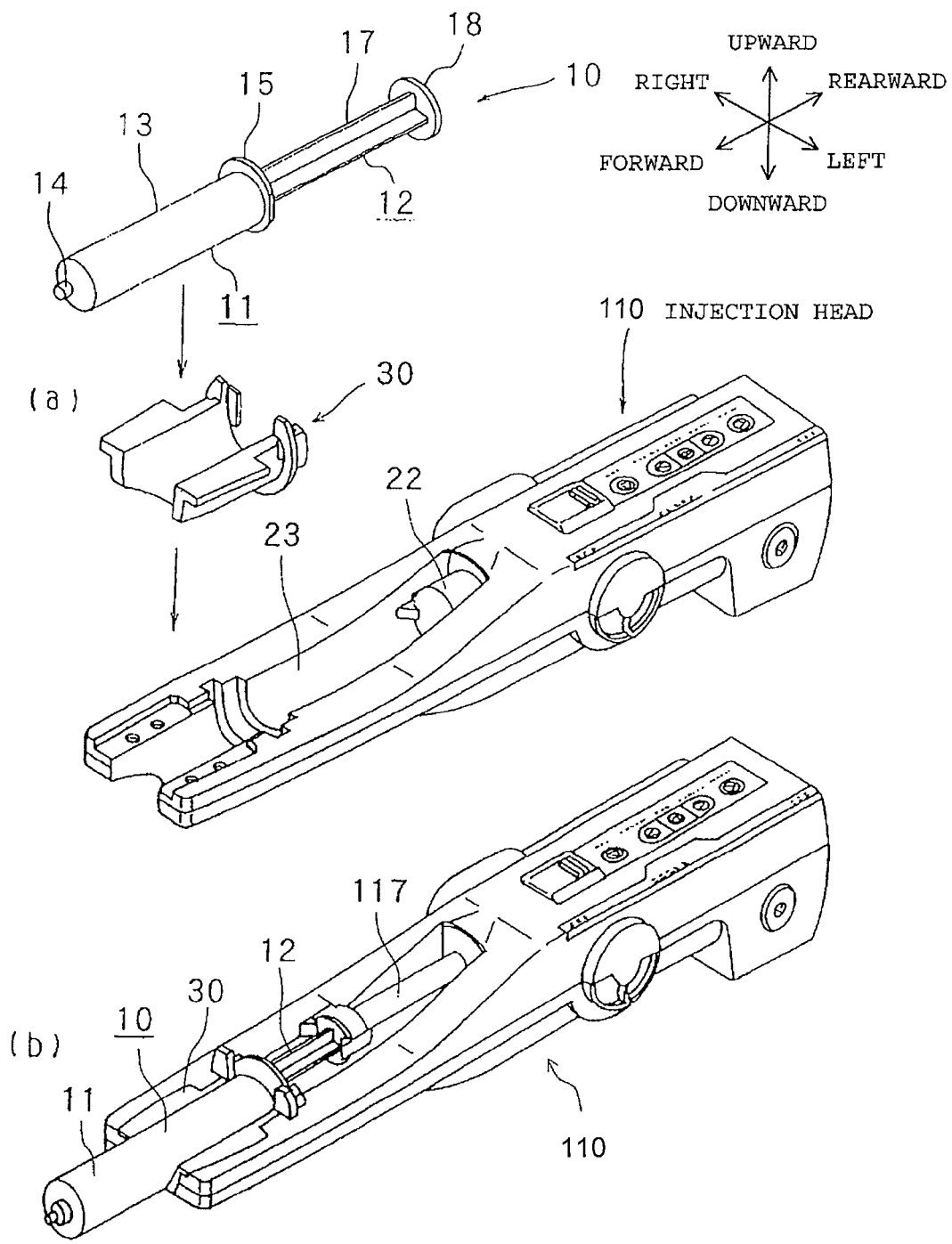
FIG. 5 is a perspective view showing the outer appearance of an injection head and a normal syringe of a chemical liquid injector.

Injection head 110 is attached to the top end of caster stand 111 by movable arm 112. As shown in FIG. 5, a head body of injection head 110 has only one concave portion 23 formed in its upper surface in a semi-cylindrical groove shape in which normal syringe 10 is removably put. In injection head 110, a cylinder holding mechanism is formed in the forward section of concave portion 23 in the upper surface for holding cylinder flange 15 of normal syringe 10. Only one piston driving mechanism 22 is placed in the rearward section of concave portion 23 for holding and sliding piston flange 18.

Piston driving mechanism 22 has a driving motor (not shown) as a driving source. The driving motor is an ultrasonic motor which is formed of nonmagnetic material such as phosphor bronze alloy (Cu+Sn+P), titanium alloy (Ti-6Al-4V), and magnesium alloy (Mg+Al+Zn) and which does not generate magnetic force affecting a magnetic field in operation.

As shown in FIGS. 1 to 4, piston adapter 200 has adapter rod 210 in an elongated shape similar to that of piston rod 17 of normal syringe 10. Adapter rod 210 has adapter flange 212 formed on the outer circumference of the rear end which corresponds to the trailing end of rod body 211.

Adapter rod 210 is formed in a hollow cylindrical shape. Elongated adapter shaft 220 is placed within adapter rod 210 to be rotatable about the same axis. Cylindrical manual operation member 230 is placed rotatably on the outer circumference near the rear end of adapter rod 210. Manual operation member 230 has a series of convex portions 231 arranged in the circumferential direction on the outer circumference to facilitate manual operation. Long hole 231 is formed in an elongated shape in the circumferential direction near the rear end of adapter rod 210. Manual operation member 230 is connected to adapter shaft 220 near the rear end thereof by connecting pin 232 passing through long hole 213 of adapter rod 210.

Adapter shaft 220 includes discoid portion 221 which serves as an engagement supporting mechanism protruding outward and which is formed integrally with the front end corresponding to the leading end. The trailing ends of elongated flange engagement members 240 are supported on the front surface of discoid portion 221 near the outer circumference thereof such that flange engagement members 240 are pivotable about the axis direction of adapter shaft 220.

Engagement open/close mechanism 250 is integrally placed on the front end of adapter rod 210 and engages with flange engagement members 240 near the leading ends thereof. More specifically, engagement open/close mechanism 250 has cylindrical member 251 mounted on the front end of adapter rod 210 and located on the outer circumference of discoid portion 221 of adapter shaft 220.

Discoid member 252 is integrally placed on the front surface of cylindrical member 251 and is located in front of discoid portion 221 and flange engagement members 240. Each flange engagement member 240 has long hole 241 opened in the axis direction of adapter shaft 220 and formed near the leading end to have the same longitudinal direction as that of its entirety. Engagement pins 253 as slide engagement members protrude rearward from the back of discoid member 252 and slidably fit into long holes 241 of flange engagement member 240.

In piston adapter 200 of the present invention, when manual operation member 230 is manually rotated relative to adapter rod 210, adapter shaft 220 and discoid portion 221 are also rotated. This rotates the trailing ends of flange engagement members 240 which engage with engagement open/close mechanism 250 near the leading ends thereof to open or close flange engagement members 240 to the axis of adapter rod 210.

Discoid member 252 has circular opening hole 254 at the center to pass through in the forward-to-rear-ward direction. Piston flange 42 of rodless syringe 40 is removably inserted into opening hole 254. Flange engagement members 240 are placed at positions where they do not obstruct opening hole 254 when they are in the opened state and at positions where they hold piston flange 42 inserted into opening hole 254 when they are in the closed state.

In piston adapter 200 of the embodiment, n flange engagement members, that is two flange engagement members 240, two discoid members 221, and two engagement open/close mechanisms 250 are placed symmetrically with respect to the axis of adapter shaft 220. Two flange engagement members 240 are pivotally supported individually on two discoid portions 221 and individually engage with two engagement open/close mechanisms 250.

The components of piston adapter 200 as described above are formed of various materials as required. Such materials are made of nonmagnetic material such as phosphor bronze alloy (Cu+Sn+P), titanium alloy (Ti-6Al-4V), magnesium alloy (Mg+Al+Zn), engineering plastic, and FRP (Fiber Reinforced Plastic).

Operation of the Embodiment

In the chemical liquid injection system of the embodiment structured as described above, when normal syringe 11 of the maximum size is used, cylinder adapter 30 is not mounted on chemical liquid injector 100. As shown in FIG. 5, when normal syringe 11 of a size other than the maximum size is used, cylinder adapter 30 is mounted on chemical liquid injector 100.

When rodless syringe 40 is used, piston adapter 200 is mounted on piston member 41 of rodless syringe 40, and as required, cylinder adapter 30 is mounted on chemical liquid injector 100. The procedure associated with the use of rodless syringe 40 in this manner will hereinafter be described in detail.

Figure 4:
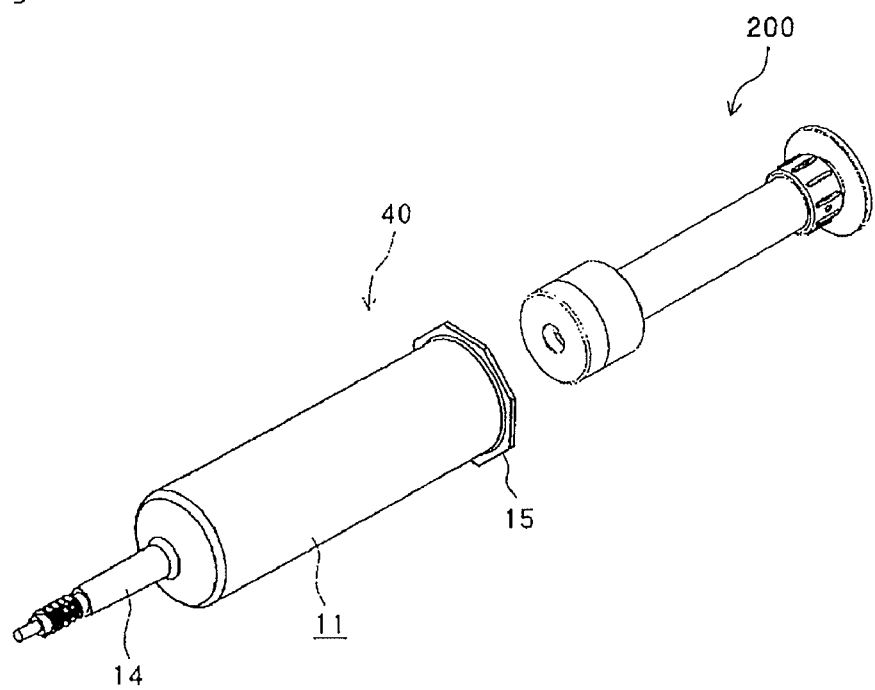
FIG. 4 is a perspective view showing the outer appearance of the piston adapter and a rodless syringe.

First, manual operation member 230 of piston adapter 200 is manually rotated clockwise to place flange engagement members 240 at the opened positions as shown in FIG. 1(a) after they are pivoted outward. In such a state, as shown in FIG. 4, rodless syringe 40 filled with a liquid is prepared. Piston flange 42 of piston member 41 located at the trailing end of cylinder member 11 of rodless syringe 40 is inserted into opening hole 254 in the front surface of piston adapter 200.

Since flange engagement members 240 located at the opened positions do not obstruct inserted piston flange 42, piston flange 42 is inserted into the position behind flange engagement members 240. Then, manual operation member 230 of the piston adapter 200 is manually rotated counterclockwise to move flange engagement members 240 to the closed positions as shown in FIG. 1(b) after they are pivoted inward.

Piston adapter 200 holds piston flange 242 by a pair of flange engagement members 240 with the front surface of piston adapter 200 in close contact with the rear surface of cylinder member 11 of rodless syringe 40. This causes piston adapter 200 to be mounted on cylinder member 11, so that rodless syringe 40 can be mounted on chemical liquid injector 100 similarly to normal syringe 10.

Conduit portion 14 of rodless syringe 40 is connected to a blood vessel of a patient through an extension tube (not shown), and rodless syringe 10 is mounted in concave portion 23 of injection head 101, such as with cylinder adapter 30 placed between them. Then, the liquid is injected into the patient in the same manner as in the related art.

Rodless syringe 40 of the pre-filled type is typically used for injection of the liquid only once. After piston member 41 is pressed into cylinder member 11, piston member 41 is not pulled out from cylinder member 11. Thus, rodless syringe 40 of the pre-filled type is formed such that it is generally easy to press piston member 41 into cylinder member 11 but it is difficult to pull piston member 41 out from cylinder member 11.

When rodless syringe 40 of the pre-filled type is used in chemical liquid injector 100, the operation is completed with piston member 41 pressed into cylinder member 11 together with piston adapter 200. In this case, the operator removes rodless syringe 40 from injection head 110 together with piston adapter 200 and manually rotates clockwise manual operation member 230 at the rear end of piston adapter 200 exposed from cylinder member 11.

Then, as shown in FIG. 1(a), flange engagement members 240 are moved to the opened positions after they are pivoted outward, so that the holding of piston flange 42 by flange engagement members 240 is released to disengage piston adapter 200 from piston member 41 inside cylinder member 11.

Effect of the Embodiment

In the chemical liquid injection system of the embodiment, piston adapter 200 is mounted on rodless syringe 40 as described above to allow rodless syringe 40 to be mounted on chemical liquid injector 100 similarly to normal syringe 10. Even when piston adapter 200 is pressed into cylinder member 11 of rodless syringe 40 together with piston member 41, piston adapter 200 is removed from piston member 41 by manually operating manual operation member 230 at the trailing end exposed from cylinder member 11.

Thus, piston adapter 200 can be pulled out easily from rodless syringe 40 without sliding piston member 41 to the trailing end of cylinder member 11. Piston adapter 200 can be repeatedly used while rodless syringe 40 can be formed as a disposable component.

In addition, in piston adapter 200 of the embodiment, flange holding members 240 are pivoted in the direction orthogonal to the slide direction of piston member 41 of rodless syringe 40 to hold piston flange 42. Even when piston adapter 200 is mounted on piston member 41 of rodless syringe 40 and slid thereon, the holding of piston flange 42 by flange holding members 240 is not released.

Chemical liquid injector 100 of the embodiment is used near MRI apparatus 300. Since piston adapter 200 is wholly formed of nonmagnetic material as described above, it does not affect the magnetic field of MRI apparatus 300. Since the driving motor of chemical liquid injector 100 is realized by the ultrasonic motor which is made of nonmagnetic material, chemical liquid injector 100 and piston adapter 200 can be used without any problem near MRI apparatus 300 in the chemical liquid injection system of the embodiment.

Modifications of the Embodiment

The present invention is not in any way limited to the abovementioned embodiment, but various changes and modifications may be made therein without departing from the scope of the invention. For example, in the above embodiment, chemical liquid injector 100 is used near MRI apparatus 300, but it can be used near a CT scanner or an angiography apparatus.

In the above embodiment, piston adapter 200 has a pair of flange holding members 240. One or three or more flange holding members 240 may be provided. However, a pair of flange holding members 240 is effective to stably hold piston flange 42 with a simple structure.

In the above embodiment, flange holding members 240 are pivotally supported on adapter shaft 220 and adapter rod 210 engages with flange holding members 240 near the leading ends thereof. However, it is possible that flange holding members 240 pivotally supported on the adapter rod and the adapter shaft engages with flange holding members 240 near the leading ends thereof (not shown).

In the above embodiment, adapter shaft 220 is fully rotatable relative to adapter rod 210. In this structure, however, adapter shaft 220 may be inadvertently rotated relative to adapter rod 210 while piston adapter 200 is mounted on rodless syringe 40, which may cause piston adapter 200 to be detached from rodless syringe 40.

If that problem should be addressed, it is preferable to provide piston adapter 200 with an engagement holding mechanism (not shown) for temporarily holding adapter shaft 220 such that adapter shaft 220 is not rotatable relative to adapter rod 210 while flange engagement members 240 are closed. Such an engagement holding mechanism may be realized by forming a convex portion formed of an elastic member to elastically protrude and retract on the outer circumference surface near the trailing end of adapter rod 210 and forming a concave portion formed in the inner circumference surface of the manual operation member 230 to accommodate and release the convex portion, for example.

In this case, adapter shaft 220 cannot be rotated inadvertently relative to adapter rod 210 while piston adapter 200 is mounted on rodless syringe 40, thereby preventing piston adapter 200 from coming off rodless syringe 40.

Figure 11:
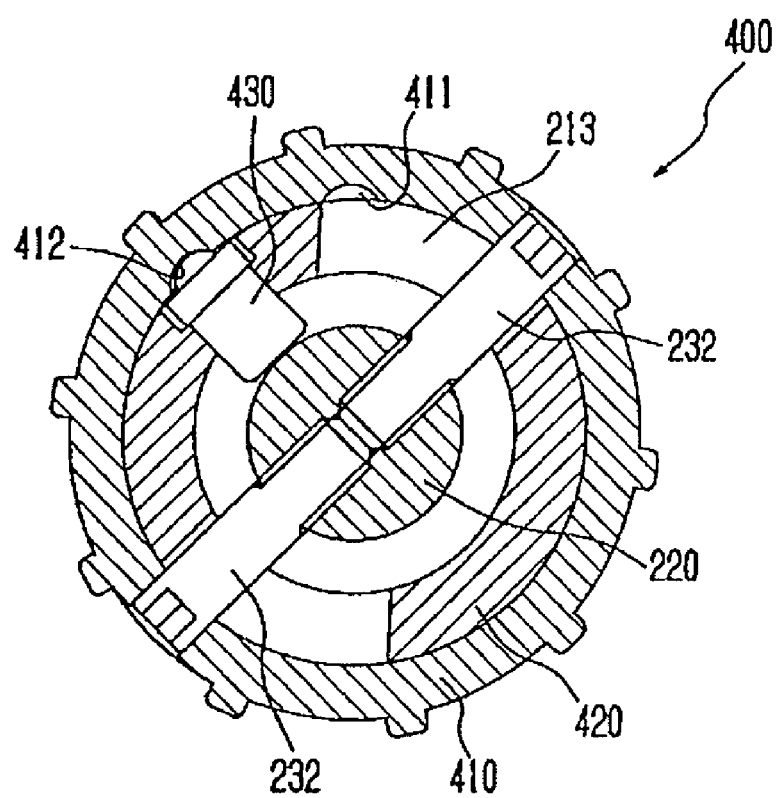
FIG. 11 is a section view showing the internal structure of the main portions of a piston adapter in a modification.
Figure 12:
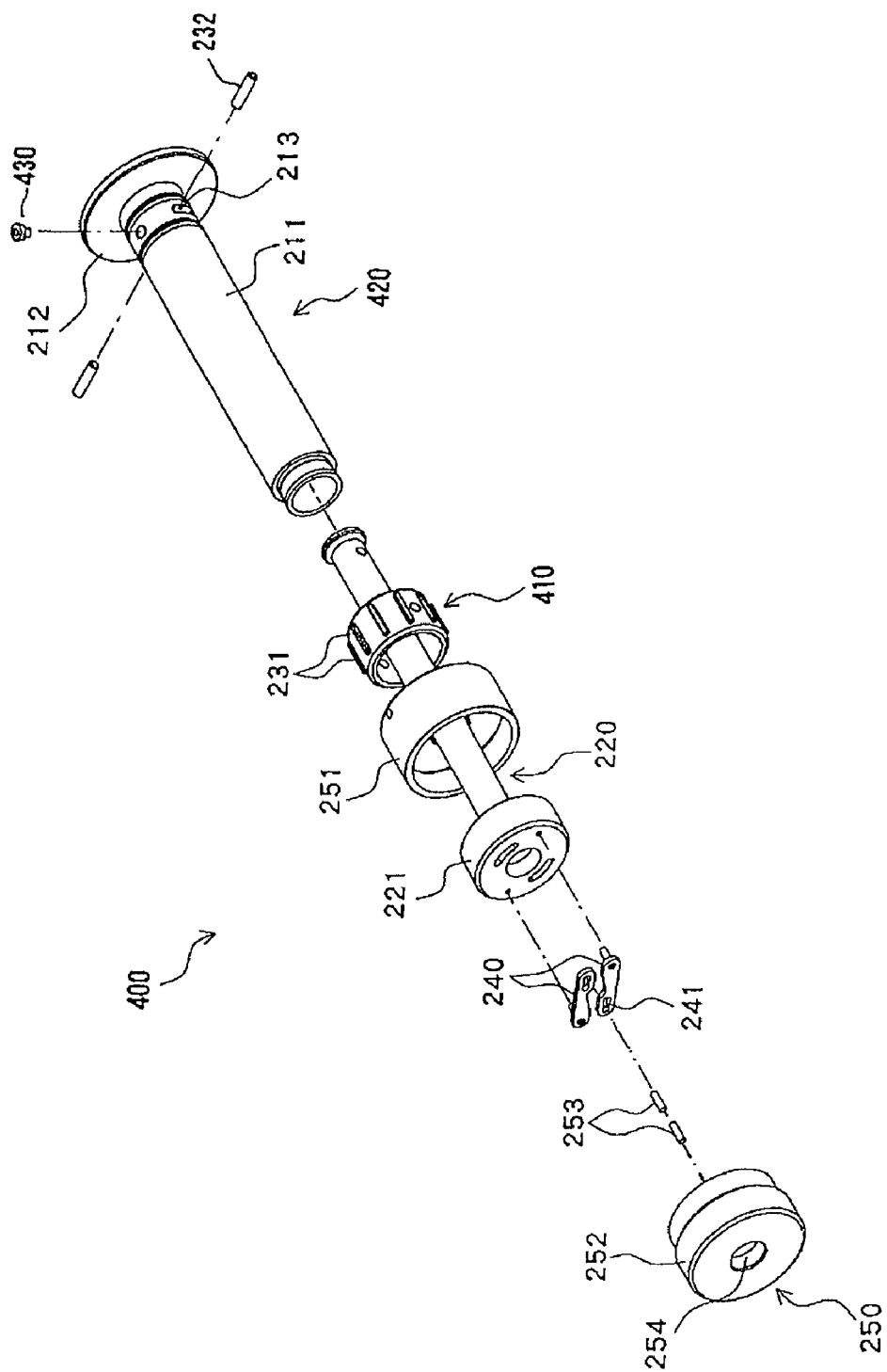
FIG. 12 is an exploded perspective view showing the structure to be assembled of a piston adapter in the modification.

More specifically, as illustrated by piston adapter 400 in FIGS. 11 and 12, concave portions 411 and 412 are formed in the inner circumference surface of manual operation member 410 and ball plunger 430 is mounted near the trailing end of adapter rod 420. In piston adapter 400 shown, ball plunger 430 is fitted into first concave portion 411 when flange engagement members 240 are opened and is fitted into second concave portion 412 when they are closed, so that flange engagement members 240 can be temporarily hold in the opened state or the closed state.

It is also possible to provide piston adapter 200 with an engagement biasing mechanism (not shown) for biasing adapter shaft 220 relative to adapter rod 210 in the direction in which flange engagement members 240 are closed. Such an engagement urging mechanism may be realized, for example, by winding a coil spring around adapter shaft 220 inside adapter rod 210 such that one end of the coil spring is connected to the inner circumference surface of adapter rod 210 and the other end is connected to the outer circumference surface of adapter shaft 220.

In this case, manual operation member 230 is manually operated to open flange engagement members 240 against the biasing of the engagement biasing mechanism, and in this state, piston flange 42 of rodless syringe 40 is inserted into piston adapter 200. Then, when the manual operation of manual operation member 230 is released, flange engagement members 240 are automatically closed by the biasing of the engagement biasing mechanism to hold piston flange 42 of rodless flange 40. The holding of piston flange 42 is maintained elastically by the biasing of the engagement biasing mechanism.

Since adapter shaft 220 is not rotated accidentally relative to adapter rod 210 while piston adapter 200 is mounted on rodless syringe 40, the removal of piston adapter 200 from rodless syringe 40 can be prevented. It is possible to use one of the abovementioned engagement holding mechanism and engagement biasing mechanism or both of them simultaneously.

In the above embodiment, flange engagement members 240 are switched between the closed positions and the opened positions by the rotation position of manual operation member 230, but this cannot be directly seen. If this represents a problem, it is preferable to provide piston adapter 200 with an open/close display mechanism (not shown) for displaying whether flange engagement members 240 are at the closed positions or opened positions.

Such an open/close display mechanism may be realized, for example, by providing a window portion formed of a through-hole or a light-transmitting plate extending from the inner circumference surface to the outer circumference surface of manual operation member 230, and forming an indicator with printing or the like on the outer circumference surface near the trailing end of adapter rod 210 such that the indicator appears through the window portion when flange engagement members 240 are at the closed positions in a different manner from that when they are at the opened positions.

In this case, the operator can simply and reliably check whether flange engagement members 240 are at the closed positions or the opened positions by seeing the indicator appearing through the window portion when he manually operates manual operation member 230. It is thus possible to prevent start of injection operation when piston flange 42 is not adequately held by flange engagement members 240.

In the above embodiment, illustrated chemical liquid injector 100 includes only one concave portion 23 and only one piston driving mechanism 22 formed in injection head 101. As shown in the related art, it is possible to provide a chemical liquid injector (not shown) which includes a plurality of concave portions 23 and a plurality of piston driving mechanisms 22 formed in the injection head.

The invention claimed is:

1. A chemical liquid injection system comprising:
   a chemical liquid injector including a piston driving mechanism of a structure for holding and sliding a piston flange of a normal syringe including an elongated cylinder member and a piston member slidably inserted into the cylinder member from an opening at a trailing end of the cylinder member, the piston member having a piston head mounted at a leading end of an elongated piston rod, the piston member having the piston flange formed on an outer circumference of a trailing end thereof;
   a rodless syringe including the elongated cylinder member and a piston member slidably inserted into the cylinder member from the opening at the trailing end of the cylinder member, the piston member not having the piston rod and having the piston flange directly formed at a trailing end of the piston head; and
   an elongated piston adapter connecting the piston flange of the rodless syringe to the piston driving mechanism of the chemical liquid injector,
   wherein the piston adapter includes:
   an elongated, hollow adapter rod having an adapter flange formed on an outer circumference of a trailing end and held by the piston driving mechanism;
   an elongated adapter shaft placed inside the adapter rod and rotatable about an axis having the same direction as that of the adapter rod;
   a rotatable manual operation member connected to a trailing end of the adapter shaft and exposed near the trailing end of the adapter rod;
   an elongated flange engagement member releaseably engaging with the piston flange of the rodless syringe;
   an engagement supporting mechanism pivotably supporting a trailing end of the flange engagement member about the axis direction at a position protruded outward from a leading end of the adapter shaft; and
   an engagement open/close mechanism connected to a leading end of the adapter rod and engaging with the flange engagement member near a leading end thereof.

2. A chemical liquid injection system comprising:
   a chemical liquid injector including a piston driving mechanism of a structure for holding and sliding a piston flange of a normal syringe including an elongated cylinder member and a piston member slidably inserted into the cylinder member from an opening at a trailing end of the cylinder member, the piston member having a piston head mounted at a leading end of an elongated piston rod, the piston member having the piston flange formed on an outer circumference of a trailing end thereof;
   a rodless syringe including the elongated cylinder member and a piston member slidably inserted into the cylinder member from the opening at the trailing end of the cylinder member, the piston member not having the piston rod and having the piston flange directly formed at a trailing end of the piston head; and
   an elongated piston adapter connecting the piston flange of the rodless syringe to the piston driving mechanism of the chemical liquid injector,
   wherein the piston adapter includes:
   an elongated, hollow adapter rod having an adapter flange formed on an outer circumference of a trailing end and held by the piston driving mechanism;
   an elongated adapter shaft placed inside the adapter rod and rotatable about an axis having the same direction as that of the adapter rod;
   a rotatable manual operation member connected to a trailing end of the adapter shaft and exposed near the trailing end of the adapter rod;
   an elongated flange engagement member releaseably engaging with the piston flange of the rodless syringe;
   an engagement supporting mechanism pivotably supporting a trailing end of the flange engagement member about the axis direction near an outer circumference of a leading end of the adapter rod; and
   an engagement open/close mechanism engaging with the flange engagement member near a leading end thereof at a position protruded outward from a leading end of the adapter shaft.

3. The chemical liquid injection system according to claim 1, wherein, in the piston adapter:
   the n flange engagement members, the n engagement supporting mechanisms, and the n engagement open/close mechanisms are arranged symmetrically with respect to the axis of the adapter shaft; and
   the n flange engagement members are individually supported pivotally on the n engagement supporting mechanisms and individually engage with the n engagement open/close mechanisms.

4. The chemical liquid injection system according to claim 1, wherein the flange engagement member has a long hole opened in the axis direction and formed near the leading end to have the same longitudinal direction as that of its entirety, and
   the engagement open/close mechanism includes a slide engagement member protruding in the axis direction to slidably fit into the long hole.

5. The chemical liquid injection system according to claim 1, wherein the piston adapter includes an engagement holding mechanism for temporarily holding the adapter shaft not to be rotatable relative to the adapter rod when the flange engagement member is closed.

6. The chemical liquid injection system according to claim 5, wherein the manual operation member is formed in a cylindrical shape having a concave portion formed in its internal circumference surface, and
the engagement holding mechanism comprises a ball plunger put on the adapter rod to releaseably fit into the concave portion of the manual operation member.

7. The chemical liquid injection system according to claim 1, wherein the piston adapter includes an engagement biasing mechanism for biasing the adapter shaft relative to the adapter rod in the direction in which flange engagement member is closed.

8. The chemical liquid injection system according to claim 1, wherein the piston adapter includes an open/close display mechanism for displaying whether the flange engagement member is at a closed position or at an opened position.

9. The chemical liquid injection system according to claim 8, wherein the adapter rod is formed in a cylindrical shape at least in its outer circumference near the trailing end thereof,
the manual operation member is formed in a cylindrical shape located on an outer circumference surface of the adapter rod, and
the open/close display mechanism includes a window portion extending from an inner circumference surface to an outer circumference surface of the manual operation member, and an indicator provided on an outer circumference surface near the trailing end of the adapter rod such that the indicator appears through the window portion when the flange engagement member is at the closed position in a different manner from that when the flange engagement member is at the opened position.

10. The chemical liquid injection system according to claim 1, wherein each of the components of the piston adapter is formed of nonmagnetic material, and
the piston driving mechanism of the chemical liquid injector includes an ultrasonic motor formed of nonmagnetic material as a driving source.

11. A piston adapter adapted for the chemical liquid injection system according to claim 1, comprising:
an elongated, hollow adapter rod having an adapter flange formed on an outer circumference of a trailing end and held by a piston driving mechanism of a chemical liquid injector;
an elongated adapter shaft placed inside the adapter rod and rotatable about an axis having the same direction as that of the adapter rod;
a rotatable manual operation member connected to a trailing end of the adapter shaft and exposed near the trailing end of the adapter rod;
an elongated flange engagement member releaseably engaging with the piston flange of a rodless syringe;
an engagement supporting mechanism pivotably supporting a trailing end of the flange engagement member about the axis direction at a position protruded outward from a leading end of the adapter shaft; and
an engagement open/close mechanism connected to a leading end of the adapter rod and engaging with the flange engagement member near a leading end thereof.

12. A piston adapter adapted for the chemical liquid injection system according to claim 2, comprising:
an elongated, hollow adapter rod having an adapter flange formed on an outer circumference of a trailing end and held by a piston driving mechanism of a chemical liquid injector;
an elongated adapter shaft placed inside the adapter rod and rotatable about an axis having the same direction as that of the adapter rod;
a rotatable manual operation member connected to a trailing end of the adapter shaft and exposed near the trailing end of the adapter rod;
an elongated flange engagement member releaseably engaging with the piston flange of a rodless syringe;
an engagement supporting mechanism pivotably supporting a trailing end of the flange engagement member about the axis direction near an outer circumference of a leading end of the adapter rod; and
an engagement open/close mechanism engaging with the flange engagement member near a leading end thereof at a position protruded outward from a leading end of the adapter shaft.

13. The piston adapter according to claim 11, further comprising an engagement holding mechanism for temporarily holding the adapter shaft not to be rotatable relative to the adapter rod when the flange engagement member is closed.

14. The piston adapter according to claim 13, wherein the manual operation member is formed in a cylindrical shape having a concave portion formed in its internal circumference surface, and
the engagement holding mechanism comprises a ball plunger put on the adapter rod to releaseably fit into the concave portion of the manual operation member.

15. The chemical liquid injection system according to claim 2, wherein, in the piston adapter:
the n flange engagement members, the n engagement supporting mechanisms, and the n engagement open/close mechanisms are arranged symmetrically with respect to the axis of the adapter shaft; and
the n flange engagement members are individually supported pivotally on the n engagement supporting mechanisms and individually engage with the n engagement open/close mechanisms.

16. The chemical liquid injection system according to claim 2, wherein the flange engagement member has a long hole opened in the axis direction and formed near the leading end to have the same longitudinal direction as that of its entirety, and
the engagement open/close mechanism includes a slide engagement member protruding in the axis direction to slidably fit into the long hole.

17. The chemical liquid injection system according to claim 2, wherein the piston adapter includes an engagement holding mechanism for temporarily holding the adapter shaft not to be rotatable relative to the adapter rod when the flange engagement member is closed.

18. The chemical liquid injection system according to claim 17, wherein the manual operation member is formed in a cylindrical shape having a concave portion formed in its internal circumference surface, and
the engagement holding mechanism comprises a ball plunger put on the adapter rod to releaseably fit into the concave portion of the manual operation member.

19. The chemical liquid injection system according to claim 2, wherein the piston adapter includes an engagement biasing mechanism for biasing the adapter shaft relative to the adapter rod in the direction in which flange engagement member is closed.

20. The chemical liquid injection system according to claim 2, wherein the piston adapter includes an open/close display mechanism for displaying whether the flange engagement member is at a closed position or at an opened position.

21. The chemical liquid injection system according to claim 20, wherein the adapter rod is formed in a cylindrical shape at least in its outer circumference near the trailing end thereof, the manual operation member is formed in a cylindrical shape located on an outer circumference surface of the adapter rod, and the open/close display mechanism includes a window portion extending from an inner circumference surface to an outer circumference surface of the manual operation member, and an indicator provided on an outer circumference surface near the trailing end of the adapter rod such that the indicator appears through the window portion when the flange engagement member is at the closed position in a different manner from that when the flange engagement member is at the opened position.

22. The chemical liquid injection system according to claim 2, wherein each of the components of the piston adapter is formed of nonmagnetic material, and the piston driving mechanism of the chemical liquid injector includes an ultrasonic motor formed of nonmagnetic material as a driving source.

23. The piston adapter according to claim 12, further comprising an engagement holding mechanism for temporarily holding the adapter shaft not to be rotatable relative to the adapter rod when the flange engagement member is closed.

24. The piston adapter according to claim 23, wherein the manual operation member is formed in a cylindrical shape having a concave portion formed in its internal circumference surface, and the engagement holding mechanism comprises a ball plunger put on the adapter rod to releaseably fit into the concave portion of the manual operation member.

* * * * *

UNITED STATES PATENT AND TRADEMARK OFFICE
CERTIFICATE OF CORRECTION

| | | |
|---|---|---|
| PATENT NO. | : 8,177,757 B2 | |
| APPLICATION NO. | : 11/720189 | |
| DATED | : May 15, 2012 | |
| INVENTOR(S) | : Shigeru Nemoto et al. | |

It is certified that error appears in the above-identified patent and that said Letters Patent is hereby corrected as shown below:

At Column 1, Line 28, Change "Thmography)" to --Tomography)--.

At Column 2, Line 50, Change "10" to --40--.

At Column 3, Line 36, Change "roddless" to --rodless--.

At Column 4, Line 6, Change "Range" to --flange--.

At Column 6, Line 8, Change "DISCORD" to --DISCOID--.

At Column 7, Line 66, Change "rear-ward" to --rearward--.

At Column 10, Line 41, Change "hold" to --held--.

Signed and Sealed this
Twenty-seventh Day of November, 2012

David J. Kappos
*Director of the United States Patent and Trademark Office*